(12) United States Patent
Liu et al.

(10) Patent No.: US 6,923,961 B2
(45) Date of Patent: Aug. 2, 2005

(54) CHEMICALLY ACTIVATED CARBOXYPOLYSACCHARIDES AND METHODS FOR USE TO INHIBIT ADHESION FORMATION AND PROMOTE HEMOSTASIS

(75) Inventors: Lin-Shu Liu, Philadelphia, PA (US); Richard Berg, Arroyo Grande, CA (US)

(73) Assignee: FzioMed, Inc., San Luis Obispo, CA (US)

(*) Notice: Subject to any disclaimer, the term of this patent is extended or adjusted under 35 U.S.C. 154(b) by 0 days.

(21) Appl. No.: 10/135,133

(22) Filed: Apr. 30, 2002

(65) Prior Publication Data

US 2003/0202970 A1 Oct. 30, 2003

(51) Int. Cl.[7] .................. A61K 38/48; A61K 31/715
(52) U.S. Cl. ................... 424/94.64; 514/54; 514/57
(58) Field of Search .................... 424/93.2, 93.21, 424/455, 456, 94.64; 514/12, 44, 54, 57

(56) References Cited

U.S. PATENT DOCUMENTS

| | | | |
|---|---|---|---|
| 5,064,817 A | 11/1991 | Yedgar et al. | 514/718 |
| 5,462,990 A | 10/1995 | Hubbell et al. | 525/54.1 |
| 5,945,100 A | * 8/1999 | Fick | 424/93.21 |
| 6,106,866 A | 8/2000 | Ranney | 424/499 |

OTHER PUBLICATIONS

Elkins, et al., *Adhesion prevention by solutions of sodium carboxymethylcellulose in the rat. I.* Fertility and Sterility, vol. 41, No. 6, 926–928, Jun. 1984.

Elkins, et al., *Adhesion prevention by solutions of sodium carboxymethylcellulose in the rat. II*, Fertility and Sterility, vol. 41, No. 6, 929–932, Jun. 1984.

Wiseman, *Polymers for the Prevention of Surgical Adhesions*, Johnson & Johnson Medical, Inc., Arlington, Texas, 369–421.

Merrill, *Poly(Ethylene Oxide) and Blood Contact, A Chronicle of One Laboratory*, 199–229.

Chaikof, *Platelet Interaction with Poly(ethylene Oxide) Networks*, AIChE Journal, vol. 36, No. 7, 994–1002, Jul. 1990.

Bottenberg, et al., *Development and Testing of Bioadhesive, Fluoride–containing Slow–release Tablets for Oral Use*, J. Pharm. Pharmacol., 43:457–464, 1991

Amiji, *Permeability and blood compatibility properties of chitosan–poly(ethylene oxide) blend membranes for haemodialysis*, Biomaterials, 16, 593–599, 1995.

Dieckman, et al., *Carboxymethylcellulose in the Free Acid Form*, Industrial and Engineering Chemistry, vol. 45, No. 10, 2287–2290.

Gurny, et al., *Bioadhesive intraoral release systems: design, testing and analysis*, Biomaterials, vol. 5, 336–340, 1984.

Chen, et al., *Compositions Producing Adhesion Through Hydration*, 163–181.

(Continued)

*Primary Examiner*—James M. Spear
*Assistant Examiner*—Blessing Fubara
(74) *Attorney, Agent, or Firm*—Fliesler Meyer LLP

(57) ABSTRACT

Carboxypolysaccharides (CPS) including carboxymethyl cellulose and their derivatives are provided that can be made into sponges, gels, membranes, particulates and other forms, for a variety of antiadhesion, antithrombogenic, drug delivery and/or hemostatic applications during surgery and pharmacological therapeutics. CPSs derivatized with primary amines can be used alone or in combination with poly(ethylene glycol) and poly(ethylene oxides) and other poly(alkylene oxides) to form materials having improved drug delivery, antiadhesion, and hemostatic uses. Applications include other types of chemical modifications of CPS to provide hydrogen, ionic, Van der Walls interactions and/or covalent bonding with drugs, biologicals and other therapeutic or diagnostic purposes.

57 Claims, 7 Drawing Sheets

OTHER PUBLICATIONS

Kulicke, et al., *Characterization of aqueous carboxymethylcellulose solutions in terms of their molecular structure and its influence on rheological behavior*, Polymer, vol. 37, No. 13, 2723–2731, 1996.

Ohno, et al., *Interpolymer Complex Formation of Polysaccharides with Poly(ethylene oxide) or Poly(1–vinyl–2–pyrrolidone) through Hydrogen Bond*, Makromol. Chem., Rapid Cmun., 2, 511–515, 1981.

Acqualon, *Sodium Carboxymethylcellulose, Physical and Chemical Properties*, Hercules, Inc., 1–27.

Didishelm, et al., *Hematologic and Coagulation Studies in Various Animal Species*, J. Lab. & Clin. Med., 866–875, Jun. 1959.

Harris, et al., *Analysis of the Kinetics of peritoneal adhesion formation in the rat and evaluation of potential antiadhesive agents*, Surgery, 663–669, Jun. 1995.

Becker, et al., *Prevention of Postoperative Abdominal Adhesions by a Sodium Hyaluronate–based Bioresorbable Membrane: A Prospective, Randomized, Double–Blind Multicenter Study*, Journal of American College of Surgeons, vol. 183, 297–306, Oct. 1996.

INTERCEED (TC7) Adhesion Barrier Study Group, *Prevention of postsurgical adhesions by INTERCEED (TC7), * an absorbable adhesion barrier: a prospective, randomized multicenter clinical study*, Fertility and Sterility, vol. 51, No. 6, 933–938, Jun. 1989.

Diamond, et al., *Reduction of adhesions after uterine myomectomy by Seprafilm* membrane (HAL–F): a blinded, prospective, randomized, multicenter clinical study*, Fertility and Sterility, vol. 66, No. 6, 904–910, Dec. 1996.

Sung, et al., *Swelling properties of hyaluronic acid ester membranes*, Journal of Membrane Science, 92, 157–167, 1994.

Braun, *Poly (Ethylene Oxide)*, Union Carbide Corporation, Union Carbide Chemical and Plastics Company, Inc., Specialty Chemicals Division, (Reprinted from Handbook of Water–Soluble Gums and Resins), pp. 19–1–19–33.

*Polyox Water–soluble Resins*, Association Compounds, Union Carbide Chemicals Division, p. 22, 1991.

*Sepra film™ Bioresorbable Membrane, Product Monograph for the Reduction of Postsurgical Adhesions*, Genzyme Corporation, 1–29, 1996.

Kitano, et al., *Viscous Carboxymethylcellulose in the Prevention of Epidural Scar Formation*, Spine, vol. 16, No. 7, Jul. 1991.

*Hercules Cellulose Gum, Sodium Carboxymethylcellulose, Chemical and Physical Properties*, Hercules, Inc., 1–31, 1984.

Takayma, et al., *Effect of Interpolymer Complex Formation on Bioadhesive Property and Drug Release Phenomenon of Compressed Tablet Consisting of Chitosan and Sodium Hyaluronate*, Chem. Pharm. Bull., 38(7), 1993–1997, 1990.

Aurora, et al., *Pathology of Peritoneal Adhesions—An Experimental Study*, Indian J. Med. Res., 62, 4, 539–544, Apr. 1974.

Harland, et al., *Polyelectrolyte Gels, Properties, Preparation, and Applications*, American Chemical Society Symposium Series, Nov. 11–16, 1990, 480.

Feddersen, et al., *Sodium Carboxymethylcellulose*, Industrial Gums, Polysaccharides and Their Derivatives, Third Edition, 537–579, 1993.

Steizer, et al., *Carboxymethylcellulose*, Handbook of Water-Soluble Gums and ResinsChapter 4, pp. 4–1–4–28, 1980.

Danishefsky, et al., *Conversion of Carboxyl Groups of Mucopolysaccharides into Amides of Amino Acid Esters*, Carbohyd. Res., 16, 199–205, 1971.

Park, et al, *Test Methods of Bioadhesion*, Bioadhesive drug delivery systems, Chapter 3, 26–168, 1990.

Tsuchida, et al., *Interactions Between Macromolecules in Solution and Intermacromolecular Complexes*, Advance Polymer Science, 45–122, 1982.

Anseth, et al., *Mechanical properties of hydrogels and their experimental determination*, Biomaterials, 17, 1647–1657, 1996.

Kofinas, et al., *Development of methods for quantitative characterization of network morphology in pharmaceutical hydrogels*, Biomaterials, Vo. 18, No. 20, 1361–1369.

Liu, L.S., et al, *Synthesis and antithrombogenicity of heparinized polyurethanes with intervening spacer chains of various kinds*, Biomaterials, 1991, vol. 12, May, 390–396.

Ito, Yosihiro, et al, *Synthesis and nonthrombogenicity of polymer membrane with surface–graft polymers carrying thrombin inhibitor*, Journal of Biomedical Materials Research, vol. 26, 1065–1080 (1992).

Woonza, Rhee, et al, In vivo *Stability of Poly9ethylene glycol)–Collagen Composites*, Journal of American Chemical Society, 1997, 420–440.

Liu, L.S., et al, *An osteoconductive collagen/hyaluronate matrix for bone regeneration*, Biomaterials 20 (1999) 1097–1108.

\* cited by examiner

Figures 2A-F

CHEMICALLY ACTIVATED CARBOXYPOLYSACCHARIDES AND METHODS FOR USE TO INHIBIT ADHESION FORMATION AND PROMOTE HEMOSTASIS

FIELD OF THE INVENTION

This invention relates to derivatized carboxypolysaccharides (CPS). Specifically, this invention relates to derivatized CPS and uses in manufacturing gels and films incorporation polyethylene oxide (PEO) for drug delivery and for antiadhesion preparations. More specifically, this invention relates to anti-adhesion and hemostatic compositions comprising composites of activated CMC and PEO.

BACKGROUND OF THE INVENTION

Bleeding during any surgical operation is a major concern. It delays surgical procedure and prolongs operation time. Significant bleeding also obstructs a surgeon's view of the surgical field. Blood transfusions or the use of blood salvage devices maybe required to compensate for blood lost during and after surgery.

It is routine to tie off large bleeding vessels, press bleeding crevices with direct pressure, use electrocautery, or block punctures with sutures. These methods are moderately successful. More recently, new methods and compositions have been devised to stop bleeding. These include matrices derived from collagen, collagen-derived materials such as Angio-Seal® (Kensey Nash Corporation) and VasoSeal® (Datascope, Inc.); Flowseal™ (Fusion Medical) and Co Stasis™ (Cohesion Tech., Inc); an the combination of thrombin with collagen or fibrinogen.

Collagen is a major structural protein in the human body. Through interaction of peptide sequences comprising the three amino acids, Arg-Gly-Asp (RDG) in the triplex polypeptide fibers of collagen with surface receptors on platelet membranes, collagen-based hemostatic reagents can activate platelets and contribute to fibrin clot formation.

Polyethylene glycol (PEG)-derived matrices, such as functionally active PEG including Focal seal™ (Focal, Inc.) are designed to form a three-dimensional hydrogel at the bleeding site, which prevents fluid loss and seals punctures. Both collagen and PEG based matrices demonstrated effective in situations of diffusion bleeding.

Thrombin triggers a cascading set of chemical reactions leading to blood clot formation. However, the use of thrombin alone is of limited efficacy in hemostasis, primarily due to a lack of a framework to which a clot can adhere. Thus, a combination of thrombin with collagen matrices can accelerate the intrinsic clotting mechanism by significantly concentrating coagulation factors at the bleeding site, thereby increasing efficacy at controlling aggressive bleeding. Examples of such products are Proceed™ (Fusion Medical Technology) and Gelfoam™ (Pharmacia and Upjohn). However, to provide desirable coagulation activity, these require mixing of thrombin with the matrix immediately prior to use in the operating room.

Carboxymethylcellulose (CMC) is a water soluble, biocompatible and bioresorbable semi-synthesized polysaccharide. The safety of commercially available CMC having high purity has been identified and approved by the Food and Drug Administration (FDA) for incorporation into many products. CMC is able to react with various polymers by way of electrostatic interaction, ionic cross-linking, hydrogen bonding, Van der Waals interactions, and physical interpenetration. Because of its safety, convenience and diversity of physico-chemical properties, CMC has demonstrated wide applications in the pharmaceutical, food and cosmetic industries.

CMC is in a larger group of polymers termed "carboxypolysaccharides" (CPS), which include, but are not limited to alginate, hyaluronic acid, carboxyethylcellulose, chitin, and the like. CPS are used in the manufacture of compositions useful for drug delivery and decreasing surgical adhesions. Schwartz (U.S. Pat. No. 5,906,997), discloses compositions and methods for decreasing post surgical adhesions using films of CPS and poly(ethylene oxide) ("PEO"). Schwartz (U.S. Pat. No. 6,017,301) discloses hydrogels of CPS and PEO, their methods of manufacture and use for decreasing adhesion formation. Schwartz (U.S. Pat. No. 6,034,140) discloses association complexes of CPS and PEO and their use in decreasing adhesions. Schwartz (U.S. Pat. No. 6,133,325) discloses anti adhesion membranes made of association complexes of CPS and PEO.

Miller (U.S. Pat. No. 6,174,999) describes methods of preparing water insoluble derivatives of polyanionic polysaccharides, which require one or more polysaccharides, a nucleophile, and an activating agent to crosslink the polysaccharide to itself and the nucleophile to the polysaccharide. The reaction is performed in the presence of hyaluronate or carboxymethyl cellulose (CMC), 1-Ethyl-3-(3-dimethylaminopropyl) carbodiimide hydrochloride ("EDC"), and a nucleophile. This patent does not describe or suggest a primary amine-derivatized polyanionic polymer as a water-soluble product, nor a diamine derivatized polysaccharide. The methods described result in water insoluble forms, because all of the components are mixed together at the same time. Thus, the disclosed compositions would not trap polyethylene oxides (PEO).

Burns (U.S. Pat. No. 6,030,958) describes crosslinking a polysaccharide, and U.S. Pat. No. 5,527,893 describes incorporating an acyl urea derivative of hyaluronic acid (HA).

Goldberg et al (U.S. Pat. No. 6,010,692) describes methods for decreasing surgical adhesions, by which tissue surfaces and surgical articles involved in the surgery are coated with hydrophilic solutions containing hyaluronic acid before the operation.

Burns (U.S. Pat. No. 5,585,361) describes methods for reducing or inhibiting platelet aggregation and adhesion by administering pharmaceutical composition containing hyaluronic acid.

Cook (U.S. Pat. Nos. 6,172,208 and 6,017,895) describe conjugation of saccharides with an oligonucleotide.

Greenawalt (U.S. Pat. No. 6,056,970) describes a hemostatic composition consisting of a bioabsorbable polymer and a hemostatic compound which is prepared in a nonaqueous solvent.

Liu (U.S. Pat. Nos. 5,972,385 and 5,866,165) disclose methods of crosslinking polysaccharides by oxidizing them to aldehydes and reacting them with proteins.

Berg (U.S. Pat. Nos. 5,470,911, 5,476,666 and 5,510,418) describes methods for crosslinking glycosaminoglycans with activated hydrophilic polymers. These patents also described crosslinking collagen to derivatized hyaluronic acid using activated hydrophilic polymers.

Liu (U.S. Pat. No. 6,096,344) described polymeric polysaccharides ionically crosslinked into spheres for drug delivery.

SUMMARY OF THE INVENTION

However, there are no easily manufactured CPS or CMC derivatives that can form covalent, ionic, or other bonds with other molecules and be biocompatible and/or bioresorbable, and be useful for a variety of therapeutic uses.

Likewise, there are no methods for manufacturing compositions having derivatized CMC or other CPS that are easy and to carry out and result in biocompatible, bioresorbable compositions.

Furthermore, there are no methods for using derivatized CMC or other CPS in polymers useful for drug delivery, hemostasis and/or adhesion prevention.

Therefore, this invention includes new types of CMC or CPS derivatives carrying active functional groups, including side chain primary amines, active aldehydes, sulfonyl groups, vinyl groups, tresyl groups, and the like. The derivatized CPSs can be manufactured using synthetic methods suited to the particular type of derivative desired. Once manufactured, derivatized CPSs can be mixed with other molecules, including unmodified CPSs or additional polymers such as polyalkylene oxides (PAOs) including polyethylene oxide (PEO), and/or pharmaceutical agents suitable for treating disorders in patients. In certain embodiments, the derivatized CPS may form bonds with the other polymer components to form a cross-linked structure which may hold drugs, and/or may have longer biological half-lives than non-covalently bonded structures. The cross-linked structures maybe incorporated into materials including membranes, gels, fibers, non-woven films, sponges, woven membranes, powders, particles or other physical forms.

When placed near a surgical site, the derivatized CPS-containing structures can provide a barrier function, decreasing the tendency of scars or adhesions to form at the site.

Compositions of this invention can be provided with one or more pharmaceutical agents, such as drugs or biological agents. The types of agents are not limited, and include vasoactive agents, hormones, nucleic acids, vectors, antiinflammatory agents and the like. In embodiments for drug delivery, derivatized CPS-containing compositions may release the drug in a more sustained fashion, thereby diminishing adverse effects of rapid alterations in the concentration of the drug.

Derivatized CPS containing compositions can be used as gels, liquids or dried as membranes, sponges or spheres. Upon application to a moist tissue, a membrane, sponge or sphere preparation can take up water, becoming gel-like. By using a higher ratio of derivatizing moiety, one can produce more highly cross-linked structures and by using a lower ratio of derivatizing moiety, one can produce structures having less cross-linking. Compositions made of derivatized CPSs can have half-lives that can be controlled, with more highly cross-linked structures having a longer half-life and less cross-linked structures having a shorter half-life. Moreover, the use of longer linkers can permit the formation of a composition having larger pores than with the use of shorter linkers. By selecting the type of derivatizing agent (e.g., amine, tresyl, aldehyde, etc.) the ratio of derivatizing agent to CPS active site (e.g., COOH residues) and the length of linkers, the physical and biological properties of derivatized CPS can be controlled to suit a particular purpose, whether antiadhesion, antithrombogenesis, and/or hemostatic. By selecting the type and size of PAO, one can provide compositions that have controllable tissue adherence, platelet adherence and/or platelet aggregation behavior. By selecting a drug for incorporation into a matrix, or added to a matrix, one can provide additional, pharmacological means for affecting adhesion formation, blood flow, bleeding or other property.

The properties of the compositions can be varied by varying the pH of the compositions. Many preparations can be desirably used having a neutral pH (i.e., a pH of about 7). However, if desired, pHs of the compositions can be higher or lower. Additionally, derivatized CPS having positively charged groups can be used to associate with negatively charged components (e.g., drugs, negatively charged proteins and the like). Similarly, CPSs having negative charges can be used to associate with positively charged components (e.g, drugs, positively charged proteins and the like).

The sites of delivery of drugs using the compositions of this invention include, without limitation, skin, wounds, mucosa, internal organs, endothelium, mesothelium, epithelium. In certain embodiments, buccal, optical, nasal, intestinal, anal, vaginal applications using compositions of this invention can be used. Furthermore, the compositions of this invention are suitable for placement between adjacent tissues for diminishing the formation of unwanted adhesions.

We also provide novel hemostatic reagents comprising conjugates of CPS derivatives having primary amine groups, for example, (CMC-N), sulfonyl groups, other charged groups and PAOs. Thrombin can be pre-loaded into the CPS-N/PAO matrices. These compositions have hemostatic activity that is greater than that for either matrices having no thrombin or thrombin alone.

BRIEF DESCRIPTION OF THE FIGURES

The invention will be described with respect to the particular embodiments thereof. Other objects, features, and advantages of the invention will become apparent with reference to the specification and drawings in which.

DETAILED DESCRIPTION

Figure 1:
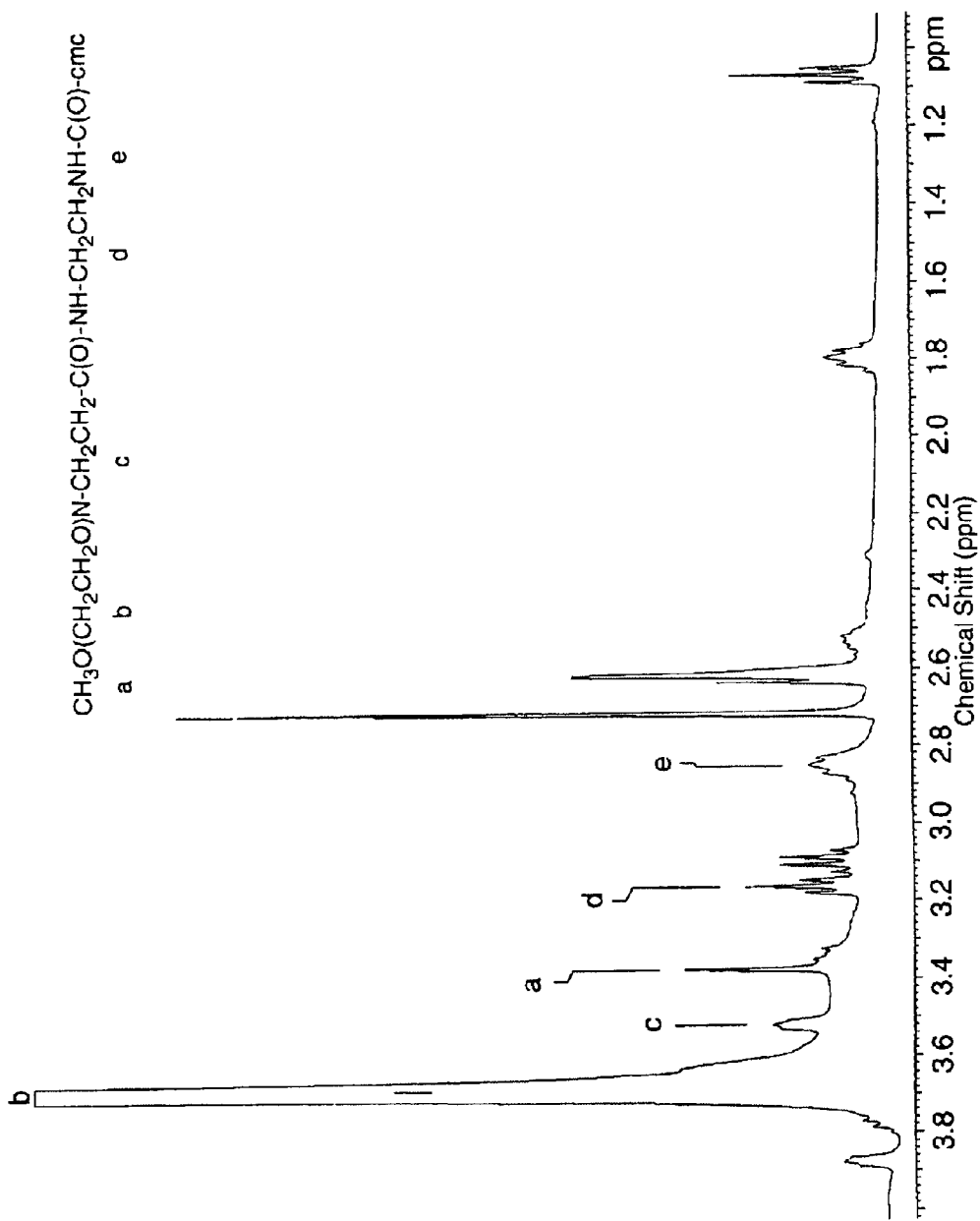
FIG. 1 depicts NMR spectra of methoxy-polyethylene oxide conjugated carboxymethylcellulose carrying primary amine groups (CMC-N/PEO) The indicated peaks a–e refer to the hydrogen atoms indicated on the insert (a, 3.379 ppm; b, 3.701 ppm; c, 3.52 ppm; d, 3.166 ppm; e, 2.862 ppm).

This invention includes a variety of derivatized CPSs, including CMCs that can interact with biologically active substances undermild conditions of pH, body or room temperatures, and/or in aqueous solutions. CMC is a polymer composed of sugar residues linked together, and each of which may have a carboxyl residue attached to the sugar moiety. There are three (3) potential sites for carboxylation on each sugar residue of CMC. Because a carboxyl residue can be chemically reactive, those locations on CMC are potential sites for derivatization. By controlling the degree of substitution (DS) of the CMC, the number of active groups on the derivatized CMC can be controlled. Derivatized CPSs and CMCs of this invention can be used for one or more of the following:

(1) as delivery vehicles for controlled release of bioactive substances, such as growth factors, active peptides, genes, cells, clotting factors such as thrombin, and antibiotics hormones including epinephrine, steroids, antiinflammatory agents and the like, and vasoconstrictors such as norepinephine and the like;

(2) as delivery vehicles for the localized release of bioactive substances, such as growth factors, active peptides, genes, cells, clotting factors such as thrombin, and antibiotics, hormones including epinephrine, steroids, antiinflammatory agents and the like, and vasoconstrictors such as norepinephine and the like;

(3) as cross-linkers for artificial extracellular matrix (ECM) construction;

(4) as binders for protein coupling and fatty absorption in both tissue engineering and food industries; and (5) as additives in food industries to produce value-added milk products.

However, it can be readily appreciated that the derivatized CPSs and CMCs of this invention can be used for a variety of purposes in which one or more physico-chemical properties are desired. Those properties include, but are not limited to bioadhesion, bioresorbability, antiadhesion, viscosity, and physical interpenetration.

I Side Chain Modification of CMC

A. CPSs and CMCs Having Primary Amines

Primary amines can be introduced to the side chains of a CPS or CMC by covalent modification of the carboxylic acids in the polysaccharide with short compounds containing primary amines at either end (e.g., diamines, such as ethylenediamine), to form an amide linkage with the carboxyl residue, leaving a free primary amine at the other end of the linker. The length of the linker can be between bout 2 and about 10 atoms, with certain embodiments having between about 3 to about 8 atoms, in alternative embodiments of between about 5 and 7 atoms, and in further embodiments, about 6 atoms. The length of the linker can be selected to provide a "loose" structure, in which relatively long linkers are used, or alternatively, a "tight" structure, in which relatively shorter linkers are used. Long linkers and loose structures may be desirable if the viscoelasticity of the composition is desired to be relatively low, where a large, biologically active agent (e.g., a protein or a gene) is to be incorporated, or in which the biological half-life is desired to be relatively short. Alternatively, short linkers and tight structures may be desirable if the viscoelasticity is desired to be relatively high (e.g., certain membranes and other solid structures), where a relatively small biologically active molecules is desired (e.g., an ion, amino acid, vitamin or pharmaceutical agent), or in which the biological half-life of the structure is desired to be relatively long. It can be appreciated that those of skill in the art can perform studies to determine the optimum length of a linker to suit a particular purpose.

To ensure that only one end of the linker is coupled to the CPS strand, one can use a molar excess (based on the degree of substitution of the CPS) of the linker. For example, one can use a molar ratio of active carboxylic acid groups to linker in the range of about 20–about 50 to provide a high degree of non-cross-linked CPS or CMC. Alternatively, by using a lower molar ratio, relatively more cross-linking between CPS molecules can be achieved. h embodiments in which a highly-cross-linked CPS is desired, one can use a relatively low (e.g., from less than about 1 to about 20) molar ratio of carboxyl residues to linkers. It can be appreciated that using a molar excess of linker molecules in a solution containing non-constrained CPS molecules (e.g., a relatively dilute solution of CPS) can promote derivatization of CPS with little cross-linking. However, in situations in which CPS molecules are constrained (e.g., high CPS concentrations) or are tightly packed together, there maybe an increased tendency for cross-links to form between different CPS chains. It can be readily appreciated that workers of skill in the art can select a molar ratio of carboxyl residues to linker molecules to produce a desired degree of cross-linked CPSs.

Amide bonds can be formed using any desired chemical interactions, including carbodiimide mediated coupling, active ester intermediates, and the use of carbonylating compounds. For some applications, it may be desirable to use 1-Ethyl-3-(3-dimethylaminopropyl)carbodiimide hydrochloride (EDC).

B. CPSs Having Active Aldehydes

In other embodiments of this invention, aldehyde groups on a CPS molecule can be produced by oxidation of the polysaccharide. In certain embodiments, it can be desirable to use a periodate such as sodium periodate. A reaction can occur between two adjacent secondary hydroxyl residues to cleave a carbon-carbon bond between them and to create two terminal aldehyde groups. The aldehyde-modified CPS can then be recovered by lyophilization and stored in a desiccator at a temperature of, for example, about 4° C. in the dark.

C. CPSs Having Active Tresyl Groups

Hydroxyl groups of polysaccharides may also be activated by certain compounds to form intermediate reactive derivatives containing leaving groups suitable for nucleophilic substitution reactions. However, hydroxyl groups of polysaccharides are only mild lynucleophilic, having a nucleophilicity about equal to that of water. To avoid hydrolysis of the active groups by cross-linking reagents, the resulting bond should desirably be stable in aqueous conditions. Sulfonyl chlorides, such as trifluoroethanesulfonyl chloride (tresyl chloride), are well suited for hydroxyl modification. The resulting CPS-sulfonyl chloride derivatives can be used for protein coupling reactions or for cross-linking.

D. CPS Having Active Vinyl Sulfone Groups

Divinyl sulfone (DVS) can be effectively used to modify hydroxyl groups of CMC and other polysaccharides. To avoid disfavored intra- and intermolecular cross-linking, DVS should be used in excess. As with the diamine linkers discussed above, the molar ratio of hydroxyl resides to linker should be chosen to provide a desired degree of non-cross-linked CPS such as a molar ratio of vinyl sulfone to hydroxyl of 30 to 1.

E. Usefulness of the Invention

Effects of the modification of CPSs such as CMC with PEO or other polyalkylene oxide (PAO) on the activation of coagulation components were evaluated by determining their effect on stimulating the intrinsic clotting pathway. The APTT procedure was used to evaluate the intrinsic clotting pathway because it is a clinically relevant test for the detection of deficiencies of coagulation factors or abnormalities in the intrinsic pathway (Imanishi, Ito et al. 1988). In certain embodiments, the presence of CMC-N matrix without the modification of PEO was most active towards the blood intrinsic coagulation system, as demonstrated by decreasing APTT values. In other embodiments, the matrix composed of CMC-N/PEO prolonged the APTT, indicating that grafted PEO suppressed the activation of coagulation factors in the intrinsic clotting pathway. These examples are illustrative of the effects derivatized CPS and PAOs. In addition to effects on platelets, proteins and clotting, PAOs can affect adherence of compositions to tissues, physical properties, including stiffness, viscosity, strength, and biological half-life, among others. By varying the composition of derivatized CPS/PAO.

It has been documented to use a PEO coating on a surface to prevent proteins or cells from depositing on the surface (Gombotz 1992). The mechanism of the effective repulsion of proteins from PEO grafted materials surface is not known with certainty, but according to one theory, the degree of conformational freedom of proteins is reduced when they are close to the PEO layer, and consequently, an entropic repulsion between the PEO and the proteins may occur (Karlström 1997). Other theories may account for the observation, and this invention is not intended to be limited to any particular theory. In certain embodiments, the PEO modified CMC matrices were less active toward the intrinsic coagulation system (Table 3) and platelets (FIG. 3, 4 and Table 3) than the unmodified CMC and CMC-N matrices. The PEO modified CMC matrices were also demonstrated to better preserve thrombin in pre-loaded matrices from deactivation during the freezing and lyophilization process (Table 4). Although the mechanisms are not well understood, according to one theory, PEO may preserve thrombin activity or alternatively, it may facilitate the release of thrombin from the matrices when contacted with fluid. Because of the desirable property of PEO on limiting protein interaction, CMC-N/PEO maybe considered an anticoagulant; however, the additional property of delivering of thrombin, matrices of CMC-N/PEO with exogenous thrombin permits a new approach to treating bleeding by providing antithrombogenic, hemostatic compositions.

The derivatized CPS-containing compositions of this invention can be made which have a wide range of physical and chemical properties. In addition to being able to vary charge, water uptake and drug association, compositions having cross-linked CPS can be formed, which can have prolonged residence times, compared to non-cross-linked compositions. Cross-linked preparations can permit the manufacture and use of the compositions for a wide variety of hemostatic and drug delivery applications.

The results of the current experiments reflect the summarization of the various parameters of the matrix, which include the hydration characteristics, the activity towards blood intrinsic coagulation cascade, the interaction with exogenous thrombin, and the mechanical strength in attaching to bleeding surfaces. Taking balance of all considerations, thrombin-loaded CMC derivatives grafting with primary amine or PEO demonstrated excellent hemostasis. In addition, the results suggest that the delivery of thrombin seems an effective strategy in the development of hemostasis.

The discoveries of this invention will be useful for drug delivery generally. CPSs at pHs above the pK of dissociation of the hydroxyl hydrogen atom, yield moieties which contain negatively charged or partially negatively charged carboxyl residues (—COO—), which can form electrostatic interactions with positively charged portions of drugs or proteins. For example, the hemostatic protein thrombin is positively charged, and can form ionically associated structures with CPS to form a delivery form of the protein. Similarly, other proteins containing positively charged amino acids, (e.g., lysine, arginine and the like) on an exterior portion of the protein can also be electrostatically bound to carboxyl groups. Even if a positively charged amino acid or other moiety on a protein is not at the surface, if interact with a negatively charged derivatized CPS, such molecules can be associated with the CPS. Certain proteins contain positively charged carbohydrate residues, such as N-acetylglucosamine, which, at physiological pH ranges can bind a hydrogen ion to produce a positively charged amino group. Such positively charged groups can be a site of association with a negatively charged derivatized or underivatized CPS.

Conversely, drugs, or proteins comprising negatively charged residues (e.g., aspartic acid, glutamic acid and the like) can become electrostatically attracted to positively charged moieties on derivatized CPSs including CMC. Certain therapeutically useful proteins, such as heparin, are glycoproteins, meaning that carbohydrate moieties are attached to the amino acid core of the protein molecule. Many of the carbohydrate moieties of glycoproteins are negatively charged, and include sialic acid, by way of illustration only. Moreover, certain glycoproteins have sulfate residues (—$SO_4$), which at many physiological pH ranges are negatively charged. Such protein/derivatized CPS formulations, either with or without added PAO can be used for direct injection of the protein to a desired site.

Nucleic acids have numerous positively charged residues on the nucleotide bases, arginine, thymine, guanine, cytosine or uracil. Thus, DNAs and RNAs maybe delivered using CPS and/or derivatized CPSs. In certain embodiments, negatively charged derivatized CPSs can be advantageously used. By way of example only, sulfonyl groups, tresyl groups and the like can be used. Moreover, underivatized CPSs at pHs at which carboxyl groups are at least partially dissociated have negatively charged moieties which can associate with positively charged nucleic acids. Such nucleic acid delivery can be useful for gene therapy, antisense nucleotide therapy, vector transfection, and viral transfection of cells in vitro.

For gene transfection, the nucleic acid may comprise a vector having a promoter region, an enhancer region and a coding region. Many such nucleic acids are known in the art, and will not be described herein further. Nucleic acids used for antisense therapeutics include DNAs or RNAs having sequences complementary to a mRNA encoding a protein whose translation is not desired. Examples include RNAs directed against viral or cellular gene sequences, as described in U.S. Pat. Nos. 5,858,998 and 6,291,438, incorporated herein fully by reference. Additional antisense nucleotides are known in the art and will not be discussed further.

It can be readily appreciated that PAOs, including PEO can be added to such delivery vehicles and thereby confer desirable properties of antithrombogenesis, decreased platelet adhesion and activation and other properties of the PAOs.

Moreover, certain drug-associated CPS can be formed and then mixed with derivatized CPS. For example, an underivatized CPS having negatively charged carboxyl moieties can be used to associate with a positively charged drug for delivery (e.g., thrombin). Addition of this material to a composition comprising a derivatized CPS (e.g., CMC-N) can provide a composition in which the drug for delivery is associated with one of the CPSs and the other CPS can confer desirable properties to the mixture (e.g, increased or decreased viscosity), which can increase the half-life of the delivered drug. It can be readily appreciated that forming an association of a derivatized CPS with a drug, and then adding underivatized CPS can provide a composition that has both desirable drug-binding features and desirable physico chemical features (e.g., increased or decreased viscosity). Furthermore, one can use different types of derivatized CPSs which can be associated with different drugs for co-delivery. For example, a negatively charged, derivatized CPS can be used to associate with a positively charged drug, and a positively charged, derivatized CPS can be used to associate with a negatively charged drug. By mixing the two combinations together, one can create compositions which provide desired pharmacodynamic properties (e.g., desired pharmaceutical effects) as well as desirable pharmacokinetic properties (e.g., tissue half-life). Thus, using mixtures of derivatized and un-derivatized CPS can provide a greater degree of flexibility in formulating drug delivery compositions.

The types of drugs or biological agents that can be advantageously delivered using the compositions of this invention are not limited. Any agent that can be used for diagnosis or treatment of a disease or condition can be delivered using the compositions of the invention, so long as the efficacy of the agent is not so reduced by association with the compositions as to render them unsuitable for their intended purposes. For example, drugs include vasoactive agents including vasodilators and vasoconstrictors, hormones, chemotherapeutic agents, growth factors, clotting factors, antibiotics, antiinflammatory agents.

It can be appreciated that the above descriptions are not intended to be limiting to the scope of the invention. Rather, they are intended to be representative of the many different embodiments of the invention.

EXAMPLES

The following examples are presented to illustrate certain embodiments of this invention, and are not intended to limit the scope to the embodiments so illustrated. Rather, workers of skill in the art can modify or adapt the teachings of this invention to make and use other variations without undue experimentation. All of those embodiments are considered to be part of this invention.

Example 1
Preparation of CMC Having Primary Amine Groups

Primary amines can be introduced to the side chains of CMC by covalent modification of the carboxylic acids (carboxylate chains) in the polysaccharide with compounds containing primary amines at either end, such as ethylendiamine (EDA), to form amide linkages. To ensure that only one end of the compound coupled to each carboxylate and does not cross-link the macromolecules being modified, the diamine should be used in excess. Amide bond formation may be accomplished by several methods including carbodiimide mediated coupling, active ester intermediates, and the use of carbonylating compounds. In this study, a water soluble carbodiimide, 1-Ethyl-3-(3-dimethylaminopropyl) carbodiimide hydrochloride (EDC), was used. A protocol is described in the following paragraph.

Materials

CMC (degree of substitution, "DS", 1.19), 3.0 g in 300 ml MES buffered saline (pH 4.7), EDA, 30.6 g in 45 ml MES; and EDC, 2.92 g in 5 ml MES.

Procedure

To the CMC solution, we added the EDC solution under constant stirring. The reaction solution was stirred at room temperature for 30 min followed by the addition of an EDA solution. After a reaction time of 48 hr, the reaction solution was transferred into a dialysis membrane tube (Spectro/Por®, MSCO, 12–14,000) and dialyzed against 4.0 L NaCl for 16 hr, then against a large volume of running de-ionized water for an additional 24 hr. The dialyzed reaction solution was lyophilized to obtain dry materials. The dry product thus formed was stored in desiccators at room 4° temperature (4° C.) for further application.

Polymer Identification

The introduction of primary amine onto CMC and the formation of CMC-N and PEO conjugate were confirmed by NMR using a Varian 400 spectrometer. Signals were referenced to tetramethyl silane (TMS). The amount of functional groups of —COOH and —$NH_2$ on CMC, CMC-N, and CMC-N/PEO was quantified by calorimetric methods using rhodamine 6 G (Liu, Ito et al. 1991) and TNBS (Ito, Liu et al. 1991), respectively.

FIG. 1 depicts the NMR analysis of a modified CMC-N of this invention. The spectrum shown indicates peaks a, b, c, d, and e along with a structure of derivatized CMC. Individual portions of the derivatized CMC are indicated, corresponding to the peaks in the NMR spectrum.

Table 1 shows the calculated and measured amounts of various moieties in matrices containing derivatized or underivatized CMC.

TABLE 1

Determination of Active Groups in CMC-Derivatized Matrices

| Samples | Calculated ($\mu$mole/mg) | | Determined ($\mu$mole/mg) | |
| --- | --- | --- | --- | --- |
| | —COOH | —$NH_2$ | —COOH | —$NH_2$ |
| CMC | 4.63 | 0 | 4.74 ± 0.14 | NF* |
| CMC-N | 4.23 | NF | 4.55 ± 0.09 | |
| CMC-N/PEO | 4.02** | NF | 4.18 ± 0.11 | |

*Not found;
**Calculated based on the mass ratio of PEO and CMC-N.
Determinations performed, n = 3.

Example 2
Viscosity of CMC-N and CMC-N/PEO Composites

Primary amine carried CMC derivatives (CMC-N) prepared from CMCs with various DS (0.8 and 1.2) and molecular weight (700K and 250K Dalton) were firstly characterized for viscosity in various formulations: (1) composite gel with PEO (CMC-N/PEO); (2) in the presence (3) in the absence of calcium ion; and (4) as a coacervate with CMC. Experiment was performed at ambient temperature using a Brookfield Digital Viscometer (Model VD-II, Brookfield Engineering Laboratory, Inc.; Stoughton, Mass.) at the shear rate of 05 and spindle #29. The pH of these materials was about 7. Results are shown in Table 2 below.

TABLE 2

Viscosity of PEO/CMC Composites

| Solution composition (%) | | | |
|---|---|---|---|
| CMC | CMC-NH$_2$ | PEO | Viscosity (cps) |
| 1.0 | 0 | 0 | $0.3 \times 10^3$ |
| 2.0 | 0 | 0 | $1.1 \times 10^3$ |
| a)2.0 | 0 | 0 | $3.4 \times 10^4$ |
| b)2.0 | 0 | 0 | $1.6 \times 10^3$ |
| 0 | 1.0 | 0 | $0.3 \times 10^3$ |
| 0 | a)1.0 | 0 | $1.2 \times 10^3$ |
| 0 | 2.0 | 0 | $0.7 \times 10^3$ |
| 1.0 | 0 | 1.0 | $0.4 \times 10^3$ |
| 0 | 1.0 | 1.0 | $0.7 \times 10^3$ |
| 0 | a)1.0 | 1.0 | $1.7 \times 10^3$ |
| 1.0 | 1.0 | 0 | $2.3 \times 10^{3*}$ |
| a)1.0 | a)1.0 | 0 | $0.9 \times 10^{6*}$ |

Unless indicated, CMC used to prepare CMC-N derivative and for the viscosity test is that with the DS of 1.19; MW, 250,000.
a)CMC with the DS of 0.8; MW, 700,000.
b)Ca$^{++}$ in present.
*The CMC/CMC-NH$_2$ mixture was prepared by mixing equal volume of 2% CMC and CMC-NH$_2$ solutions. The mixture was allowed to stand at room temperature for 5 minutes prior to test.

We observed that the solutions of underivatized and derivatized CMC had substantially the same viscosity. However, we unexpectedly found that the addition of PEO to either the CMC or CMC-N preparations had different effects. Adding PEO to CMC altered viscosity slightly (from 0.3 to 0.4×10$^3$ cps), whereas adding PEO to CMC-N increased viscosity substantially more (from 0.3 to 0.5×10$^3$ cps). Thus, one can vary the composition of a matrix to provide a desired viscosity, depending upon the particular drug delivery or hemostatic needs.

Example 3

Tissue Adhesiveness of CMC-N/PEO Composites

The tissue adhesive property of gels was determined by measuring the force needed to detach the gels from the membrane using a modified Tape loop Tack Tester (Model LT-100; ChemInstruments, Fairfield, Ohio) equipped with a digital force meter (Chatillon Model DFM; Greensboro, N.J.). Membranes of porcine intestine were used as the receiver. The membranes were mounted onto each surface of both the test panel and specimen jaw, which was attached to the tension head by means of any a yoke and a release pin. The gap between the two membranes was adjusted to 2±1 mm by releasing and tightening the release pin. 5.0±0.1 ml of the gel were applied on the membrane bound to the test panel. All measurements were performed on settings as:
Specimen jaw lowering speed: 9 mm/s
Contact time: 3 minutes
Contact area: 5.31 cm$^2$
Specimen jaw withdrawal rate: 9 mm/s
Withdrawal height: 4.5 cm
Each experiment was carried out five times. The force (N) needed to detach the gel was recorded and represented as the mean value with standard deviation. Results are shown in Table 3 below.

TABLE 3

Tissue Adhesive Properties of PEO/CMC Composites

| Solution composition (%) | | | Peak detachment force |
|---|---|---|---|
| CMC | CMC-NH$_2$ | PEO | (N) |
| 1.0 | 0 | 0 | 0.12 ± 0.01 |
| 2.0 | 0 | 0 | 0.33 ± 0.01 |
| a)2.0 | 0 | 0 | 0.65 ± 0.02 |
| b)2.0 | 0 | 0 | 0.49 ± 0.01 |
| 0 | 1.0 | 0 | 0.19 ± 0.04 |
| 0 | a)1.0 | 0 | 0.19 ± 0.07 |
| 0 | 2.0 | 0 | 0.46 ± 0.13 |
| 1.0 | 0 | 1.0 | 0.15 ± 0.03 |
| 0 | 1.0 | 1.0 | 0.24 ± 0.04 |
| 0 | a)1.0 | 1.0 | 0.37 ± 0.01 |
| 1.0 | 1.0 | 0 | 0.76 ± 0.14* |
| a)1.0 | a)1.0 | 0 | 1.12 ± 0.09* |

Unless notice, CMC used to prepare CMC-N derivative and for the tissue adhesion test is that with the DS of 1.19; MW, 250,000.
a)CMC with the DS of 0.8; MW, 700,000.
b)Ca$^{++}$ in present.
*The CMC/CMC-NH$_2$ mixture was prepared by mixing equal volume of 2% CMC and CMC-NH$_2$ solutions. The mixture was allowed to stand at room temperature for 5 minutes prior to test.

As shown in Table 3, these results show that adding CMC and CMC-N together increase tissue adhesiveness more than expected based on the individual tissue adhesivenesses. This indicates synergistic actions between CMC and CMC-N. One possible theory for this interaction is that the CMC and the CMC-N form a coacervate, thereby stabilizing the composition, and can therefore increase the time needed for the composition to dissolve in body fluids.

Example 4

PEO and CMC Released from CMC-N/PEO Composites

Studies on the release of CMC and PEO from gels were performed using PBS as release medium. Membranes of porcine intestine were mounted on the bottoms of a petri dish (g=50 mm) using double side adhesive tape. An aliquot of 5.0 ml of each gel was evenly spread over the surface of the membrane. PBS, 10 ml, was carefully loaded on the top of the gel layer followed by incubation at room temperature under gentle shaking. At the time periods of 3, 10, 20 min, 1 h and 2 h, the dish was tipped to one side and 1.0 ml of the incubation solution was pipetted from the solution above the gel and analyzed for the amount of PEO and CMC released.

The released PEO was quantified by measuring the absorbance of the fluorescein moiety attached at the PEG chain at 500 nm. CMC amount in the incubation solution was determined by measuring the absorbance at 480 nm after incubating with phenol and sulfuric acid at 30° C. for 20 minutes. Results are shown in Table 4 below.

TABLE 4

Amounts of Gel Components Released Into Medium

| Incubation time | PEO (mg) released from | | CMC (mg) released from | |
|---|---|---|---|---|
| (min) | CMC/PEO | CMC-N/PEO | CMC/PEO | CMC-N/PEO |
| 3.0 | 0.22 ± 0.11 | 0.28 ± 0.15 | ND* | ND |
| 10.0 | 0.30 ± 0.10 | 0.28 ± 0.17 | ND | ND |
| 20.0 | 1.04 ± 0.18 | 0.59 ± 0.09 | ND | ND |
| 60.0 | 5.07 ± 0.69 | 2.24 ± 0.21 | 4.03 ± 0.21 | 2.15 ± 0.19 |

*ND, Not detectable.

Example 5

Stability of CMC/CMC-N Polyelectrolyte Gels

CMC/CMC-$NH_2$ coacervate gel was prepared by mixing equal volume of 2% CMC and CMC-$NH_2$ solutions under vigorous stirring at room temperature. Upon mixture, a white precipitate was observed, indicating the formation of coacervate. The precipitate was allowed to grow and stabilize at room temperature for 5 min. followed by centrifugation at 1,500 rpm for additional 5 min. The precipitate thus formed was incubated with D.I. $H_2O$, PBS, and tissue culture medium, Dulbecco's Modified Eagle's Medium (DMEM, Sigma Chemical, San Luis) at ambient temperature for two weeks. CMC with different DS and the gel of CMC cross-linked with calcium were used as control. The stability of each sample was judged by eye observation and subjectively graded on the scale of 1 (dissociate easily), 2 (partially dissociate in two weeks), and 3 (stable for two weeks). Results are shown in Table 5 below.

TABLE 5

Stability of CMC/CMC-N Composites

| Media | a)CMC/Ca++ | a)CMC | b)CMC | b)CMC/CMC-N |
|---|---|---|---|---|
| D.I. $H_2O$ | 1 | 1 | 1 | 3 |
| PBS | 1 | 1 | 1 | 2 |
| DMEM | 1 | 1 | 1 | 2 | a)CMC with the DS of 0.8; MW, 700,000.
b)CMC with the DS of 1.19; MW, 250,000.

Example 6

Preparation of CMC-N Cross-Linked Membranes

CMC-N, 3.0 g dissolved in 15.0 ml D.I. water. The solution was cast on aperi dish (100×15 mm) and placed in a hood at room temperature for 2 days to air-dry. The membrane thus obtained was placed in an isopropyl alcohol/$H_2O$ solution containing 0.5% glutaraldehyde, shaken gently for 6 h followed by washing with 3×50 ml D.I. water, then air-dry. The cross-linked CMC-N membrane is stable in D.I. water, PBS, 1.0 N NaCl, and tissue culture medium.

Example 7

Preparation of CMC-N Cross-Linked Sponge

CMC-N, 3.0 g was dissolved in 15.0 ml D.I. water. The solution was cast on a petri dish (100×15 mm) and submitted to freeze drying. The dry product thus obtained is a sponge-like porous matrix. The matrix was placed in an isopropyl alcohol/$H_2O$ solution containing 0.5% glutaraldehyde, shaken gently for 6 h followed by washing with 3×50 ml D.I. water, then re-lyophilized. The cross-linked CMC-N porous matrix is stable in D.I. water, PBS, 1.0 M NaCl, and tissue culture medium.

Example 8

Preparation of CMC-N Cross-Linked Particles

CMC-N, 3.0 g was dissolved in 15.0 ml D.I. water. To the solution, we added with 0.1 g of disuccinimidyl suberate in 2.0 ml dimethyl sulfoxide (DSS/DMSO) under vigorous stirring. Precipitates appeared shortly after mixing. The reaction was carried out under stirring for 6 h, then standing on the bench for 24 h. The supernatant was discarded and the solid was washed three times with large volumes of D.I. water. CMC-N particles cross-linked with DSS thus formed is stable in water, saline, and tissue culture medium.

II. Hemostatic Derivatized CMC/PEO Composites

Derivatized CMCs of this invention can be very desirable as hemostatic agents. CMC/PEO composites can be manufactured as described above and used as is, or can have hemostatic factors incorporated therein. In certain embodiments, thrombin can be advantageously incorporated into hemostatic products to slow aggressive bleeding and promote clot formation.

Example 9

Modification of CMC with Ethylenediamine

Materials

Carboxymethyl cellulose (CMC) having an average molecular weight of 250 k daltons (kdal) and the degree of substitution of 1.19 was obtained from Hercules Inc. (Wilmington, Del.). 1-Ethyl-3-(3-dimethylaminopropyl) carbodiimide (EDC), ethylenediamine dihydrochloride EDA), activated partial thromboplastin time reagent (APTT), and thrombin were purchased from Sigma Chemical Co. (St. Louis, Mo.). Polyethylene glycol derivative, methoxy-PEO-SPA (mPEO-SPA, M.W. 5 kD) was obtained from Shearwater Polymers (Huntsville, Ala.). Fresh porcine skin was from a local market.

Citrated bovine blood was prepared by mixing one part of sodium citrate solution with nine parts of whole blood from a healthy adult bull (courtesy of Dr. William Plummer of the Animal Science Department, California Polytechnic State University, San Luis Obispo, Calif.).

Polymer Modification

A. Modification of CMC with Ethylenediamine

Introduction of primary amine groups into CMC was conducted according to published methods (Liu, 1991). Briefly, to a CMC solution, 0.30 ml of a solution of MES buffer, pH 4.7, was added with EDC (0.29 gm) in 2.0 ml MES, under constant stirring. The reaction solution was stirred at room temperature for 30 minutes, followed be the addition of EDA (3.0 gm) in 8.o ml MES buffer. After 48 hours, the reaction solution was transferred into a dialysis membrane tube (Spectro/Por®, M.W. cutoff: 12,000–14,000 daltons) and was dialyzed against 1 N NaCl (4.0 L) for 16 hours, then against a large volume of running de-ionized (DI) water for an additional 24 hours. The dialyzed solution was lyophilized to obtain a dry preparation of CMC derivative and was processed for the quantification of introduced primary amines to form aminated CMC (CMC-N). The dry product thus formed was stored in a dessicator at 4° C. for the following experiments.

Example 10

Conjugation of CMC-N with mPEO-PSA

PEO was grafted onto the side chains of CMC-N by the method described previously (Rhee W 1997), wheren mPEO-SPA, 0.5 g in 5.0 ml of 30.0 mM HCl, was mixed with 100.0 ml of CMC-N solution containing 1.50 g of CMC-N in 10.0 mM NaOH (mole ratio of succinimidyl to primary amine: 1.5/100) undervigorous stirring at room temperature for 24 h. The reaction solution was dialyzed against running deionized water for 24 h using Spectro/Por® dialysis membrane tube (MW cut off, 12–14,000), then lyophilized to produce CMC-N and PEO conjugate, CMC-N/PEO.

Example 11

Matrix Fabrication

Matrices of CMC, CMC-N and CMC-N/PEO composites were fabricated by loading solutions of the polymers (1.0% weight/volume in DI water) into a 96-well tissue culture plate (100 μL/well), and were frozen at a temperature of −10° C.

To determine activated partial thrombin time (APPT), matrices were prepared by casing the polymer solutions of CMC, CMC-N and CMC-N/PEO composites in glass tubes (16×125 mm; 4.0 ml pertube). The tubes were placed in a vacuum-oven and dried at a temperature of 37° C. at a pressure of $1 \times 10^{-2}$ Torr for 72 hours.

To study platelet adhesion and aggregation, matrix materials were cast onto micro cover glass plates (Van Waters & Rogers, 18 mm diameter, 2.0 ml/cm$^2$) and then air dried. To evaluate water uptake and the potential for stopping spurting bleeding, matrices were prepared by freezing each polymer solution (5.0 ml, 1% weight/volume in DI water) in a 15 ml polypropylene tube and then freeze dried.

Thrombin was incorporated by pipetting 80 μL of reconstituted thrombin solution (500 U/ml, in Tris-HCl buffer, pH 5.0) onto dried matrices. The process was performed at 4° C. to minimize loss of thrombin activity. Thrombin-loaded matrices were then lyophilized and stored desiccated at a temperature of −4° C. for further application.

Example 12

Evaluation of Structure of CMC/PEO Composites

To evaluate the structures of CMC/PEO composites of this invention, CMC, CMC-N and CMC-N/PEO matrices were studied using a scanning electron microscope (SEM; model S-806, Hitachi Ltd., Tokyo, Japan). Dried matrix specimens were coated with a thin layer of platinum (Pt; 15 nm) using an ion coated (Polaron SEM coating system, Tousimis Research Corporation, Rockville, Md.) with settings as follows: pressure: 0.5 mbar; current: 20 mA; coating period: 60 sec. The coated specimens were examined at 15 K V accelerating voltage.

To determine internal structure of matrices, dried matrices were also frozen and fractured at a temperature of −78° C., coated with Pt, then examined by SEM as described above.

Despite differences in the chemical compositions and methods of fabrication of the matrices, all CMC-derived materials had similar general external and internal surface morphology. They were highly porous, having a open pore structure. All pores were channeled with each other, resulting in a sponge-like network of sinuses within the matrices. Structural characteristics were created by controlling the lyophilizing conditions, because matrices were pre-swelled in a continuous aqueous phase, which was removed during the freeze-drying process. Although the general morphology of the matrices have similarities, there are differences, which may account for different properties of the matrices.

Figure 2A:
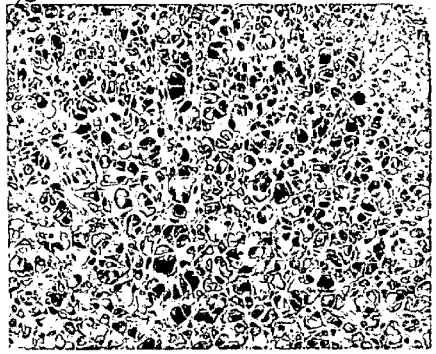
FIG. 2 depicts a scanning electron micrographs of external structures A, B and C and internal structures D, E and F of matrices prepared in microtiter plates. Matrices shown in panels A and D are made from CMC, matrices shown in panels B and E are made from CMC-N, and matrices shown in panels C and F are made from CMC-N/PEO. Magnification, 40× (A, B and C); 200× (D, E and F).
Figure 2D:
Figure 2B:
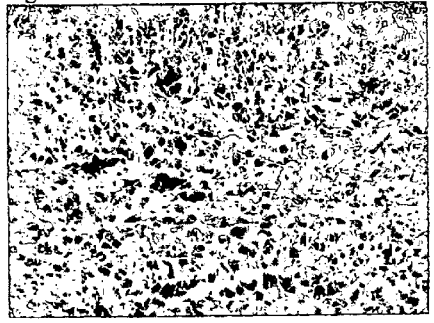
Figure 2E:
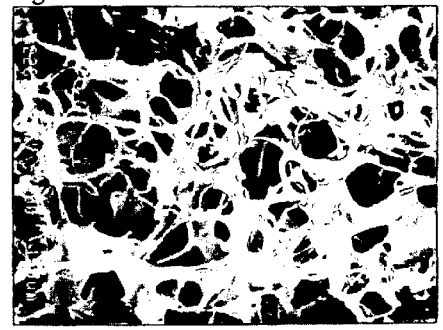
Figure 2C:

An example of a scanning electron micrograph of a Pt-coated matrix is shown in FIGS. 2A–2F. In FIG. 2A, the surface of a CMC matrix has numerous pores (Magnification: 400×). The surface of an CMC-N matrix is shown in FIG. 2B. In contrast, FIG. 2C shows that the surface of a CMC-N/PEO matrix has large and irregularly shaped pores. One theory which may account for this observation is that there are weaker interactions between the polymers of the CMC-N/PEO matrix compared to the relatively stronger interactions between CMC and CMC-N polymers in those matrices without PEO (e.g., FIGS. 2A and 2B).

Figure 2F:
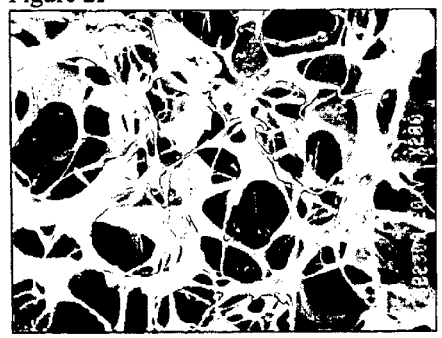

The internal structure of a CMC matrix is shown in FIG. 2D, at a magnification of 200×. FIG. 2E shows the internal structure of an CMC-N matrix, and has larger internal pores than the corresponding CMC matrix. FIG. 2F shows the internal structure of CMC-N/PEO matrix, which has large, irregularly shaped open areas.

Of particular and unexpected interest was the finding that the pure CMC matrices have the smallest overall pore size (e.g., see FIG. 2D), with the CMC-N matrices having an intermediate pore size (e.g., FIG. 2E), and the CMC-N/PEO matrix having the largest pore size.

These results indicate that matrices having smaller pore sizes can bind materials within the matrix more tightly than matrices having larger pore sizes. Because it one can alter pore size by selecting conditions of polymer concentration, type of polymer, extent of cross-linking and other factors, one can select a matrix type that best suits the needs of the particular application.

Example 13

Water Uptake

Swelling behavior of matrices of various compositions was evaluated by measuring the speed and amount of water uptake. Matrix specimens were immersed in DI water, and the time required for the swelling to reach a steady state was recorded, and the water uptake by each type of specimen was measured according to methods described previously (Liu 1999). Prior to experiments, matrix specimens were dried at 102° C. at a pressure of $1 \times 10^{-2}$ Torr in a vacuum-oven for 72 hours, and the weight, Wd, was determined using an analytical balance. After incubation in water, the adherent water was removed by placing the wet specimens on a glass plate, tipping the plate at an angle of 60° for 2 min, tapping the specimens with tissue pledgets (Kimwipes™), and the weight of the wet matrix, Ww, was recorded. The water content was calculated and expressed as (Ww−Wd)/Ww, and swellability, Ws/Wd.

We found significant differences among matrices having different chemical compositions (Table 6).

TABLE 6

Swellability of CMC-Derivatized Matrices

| Matrices | Time required for equilibrium (min.) | $(W_w - W_d)/W_w \times$ 100% | $W_w/W_d$ |
|---|---|---|---|
| CMC | 3–4 | 85.3 ± 2.6 | 7.1 |
| CMC-N | 2–3 | 89.3 ± 3.7 | 9.1 |
| CMC-N/PEO | <1 | 93.4 ± 4.3 | 15.1 |

Data presented as mean value with standard deviation (n = 5).

Table 6 shows that matrices prepared from primary amine-containing CMC (CMC-N) had a faster and higher water uptake compared to matrices prepared from unmodified CMC. The increase in swelling speed was even more pronounced for CMC-N/PEO composites, indicating that the CMC-N/PEO composites behave better than the others in terms of the extent of fluid uptake and the rate of fluid uptake.

III. Hemostatic Properties of CMC-N/PEO Composites

Hemostatic properties of CMC-N/PEO composites were determined using methods described below.

Example 14

Activated Partial Thromboplastin Time

Effects of matrices on intrinsic blood coagulation was determined using the activated partial thromboplastin time (APTT) test, using APTT reagent, Alexin™. Samples of citrate-treated, platelet poor plasma (PPP) (0.5 ml) each were placed in a glass tube pre-coated with a matrix material, followed by incubation at 37° C. for 3 min. To the plasma sample, we then added 0.5 ml of the APTT reagent and the mixture incubated for an additional 3 minutes. Then, 0.5 ml of a solution of a 20 mM $CaCl_2$ was added to the mixture, and the time required for a clot to form was recorded. Table 7 shows results of these studies.

TABLE 7

Activated Partial Thromboplastin Time (APTT)

| Samples | APTT (sec.) |
| --- | --- |
| CMC | 32 ± 4 |
| CMC-N | 22 ± 5 |
| CMC-N/PEO | 43 ± 2 |
| Glass | 33 ± 2 |

Data presented as mean value with standard deviation (n = 5).

We found that CMC-N was more effective on the intrinsic coagulation system than either CMC alone or CMC-N/PEO. Thus, incorporation of PEO into a matrix suppressed activation of intrinsic coagulation.

One theory to account for the results is that thrombin can be held by the matrices, and was therefore can be unavailable to participate in coagulation, which involves many different chemicals and substrates in the liquid medium. By decreasing the availability of thrombin (a protein) to the liquid medium outside the matrix, the rates of clotting reactions may be slowed. CMC matrices contain numerous carboxylic acid residues which may bind to thrombin. Thus, according to this theory, with the reduction in the number of free and available COOH groups on CMC, by either derivatization with amines or with formation of complexes containing PEO or PEGs, less thrombin binding can occur, thereby promoting the release of thrombin into the liquid medium, thereby promoting clotting.

Another theory which may account for the observations is that CMC matrices have smaller pores than those of either CMC-N or CMC-N/PEO matrices. FIGS. 3a–3f show that PEO-containing matrices have larger pores that can be less effective at trapping thrombin or other molecules of similar size and physical characteristics as thrombin.

Example 15

Effects of Matrix Materials on Platelet Aggregation, Adhesion and Activation Effects of matrix materials on platelet adhesion and aggregation were determined using platelet rich plasma (PRP), which was prepared from citrated whole bovine blood. Citrated blood was centrifuged at 800–1000 revolutions per minute (rpm) for 10 minutes, the supernate was collected and further centrifuged at 3000 rpm for 5 minutes to obtain platelet pellet and platelet poor plasma (PPP). The platelet pellet was dispersed in the PPP to yield a platelet suspension containing platelets at a concentration of 30–35× $10^4/\mu L$.

Platelet aggregation initiated by matrix materials was determined by measuring the time course of the optical density of PRP, beginning at the time of addition of solutions of matrix materials. Briefly, aliquots of CMC, CMC-N and CMC-N/PEG solutions containing thrombin (100 $\mu L$; 250 $\mu g$; 4U/ml PBS) was added to 2.5 ml PRP in a UV spectrophotometer tube, and the optical density (OD) was monitored at a wavelength of 580 nm at room temperature under constant stirring using a UV spectrometer (model 160U, Shimadzu, Japan) equipped with a magnetic stirrer. In another experiment, matrix materials and thrombin were tested separately for their abilities to initiate platelet aggregation.

Platelet adhesion and activation of adherent platelets were determined by counting the number of platelets adhered to the surfaces of matrices and by analyzing the morphology of adherent platelets using SEM. Plates cast from each matrix material were incubated with PRP, one piece per 2.0 ml, in borosilicate glass vials at a temperature of 37° C. After 20 minutes, the plates were washed with 0.1 M cacodylate buffer for a total of 3 times, then fixed by immersion in a cacodylate buffered solution containing 2.0% glutaraldehyde for 3 hours. The fixed plates were dehydrated in graded ethanol solutions, submitted to critical point drying using liquid $CO_2$ as a transition fluid, coated, then examined by SEM for the numbers of adherent platelets and the extent of activation.

Figure 3A:
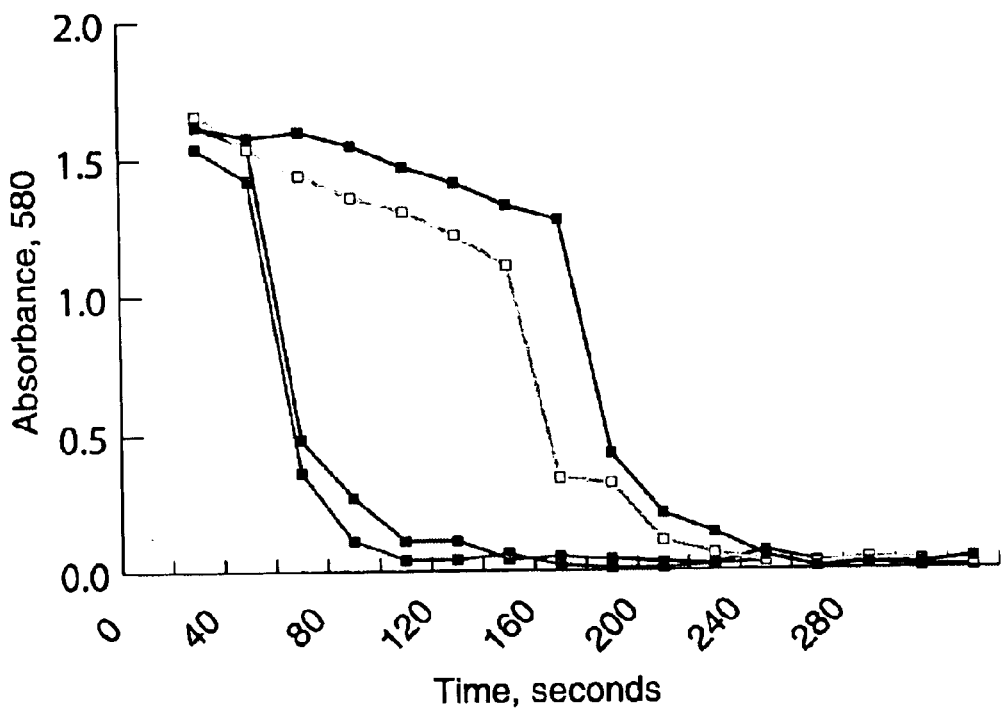
FIG. 3 depicts results of studies of platelet aggregation induced by matrix materials (25 $\mu$g/ml) in the presence (top graph A) and absence (bottom graph B) of thrombin (4 U/ml): CMC (●), CMC-N (■), CMC-N/PEO (▲), and control (○). Matrices were prepared in microtiter plates. Platelets were prepared from citrated whole bovine blood at a concentration of 30–35×10$^4$/$\mu$l.
Figure 3B:
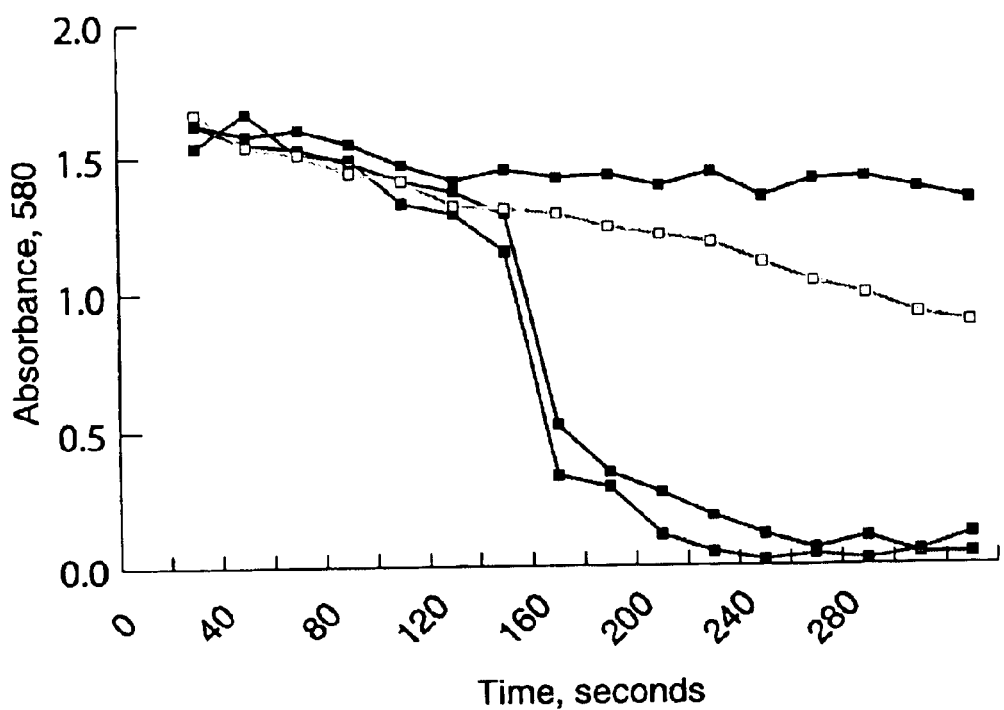

FIGS. 3A and 3B depict results of studies of platelet aggregation induced by matrix materials (25 $\mu g/ml$) in the presence (top graph A) and absence (bottom graph B) of thrombin (4 U/ml): CMC (●), CMC-N (■), CMC-N/PEO (▲), and control (○). Matrices were prepared in microtiter plates. Platelets were prepared from citrated whole bovine blood at a concentration of 30–35×$10^4/\mu l$. The vertical axis represents turbidity of the solution, as measured by optical density measured at a wavelength of 580 nm. As the platelets aggregate, the optical density decreases.

Figure 4A:
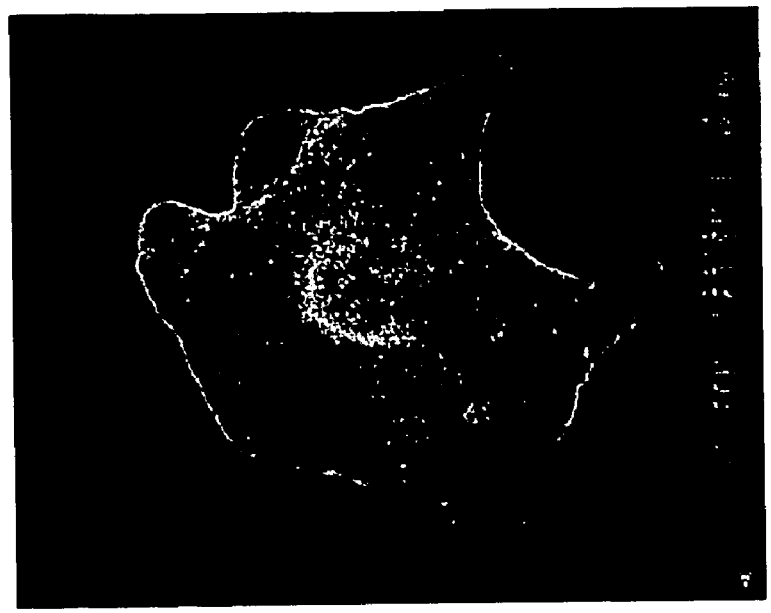
FIG. 4 depicts results of studies of activation of platelets adhered on plates coated with matrix materials as indicated in the different panels A, B, C and D. Panel A: CMC, panel B: CMC-N, panel C: CMC-N/PEO, and panel D: control. Plates (diameter, 18 mm) cast with each matrix were incubated with 2.0 ml of platelet rich plasma having a platelet concentration of 30–35×10$^4$/$\mu$l at 37° C. for 20 min.
Figure 4B:
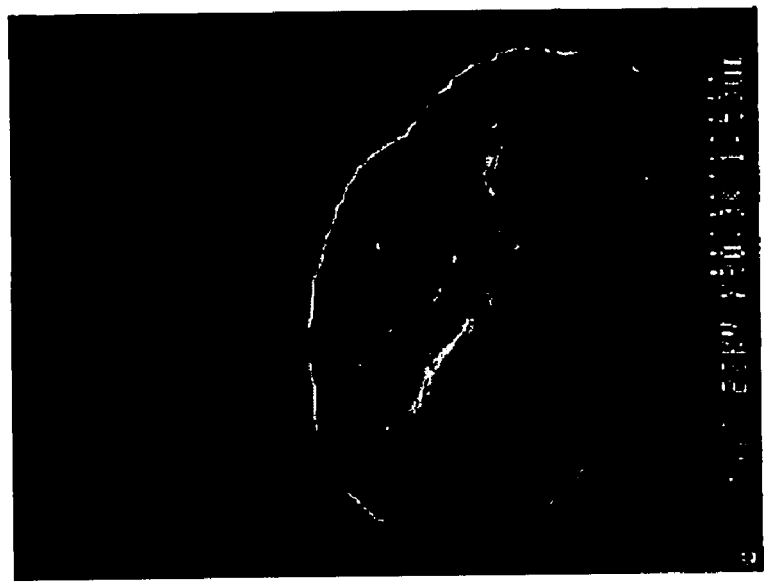
Figure 4C:
Figure 4D:
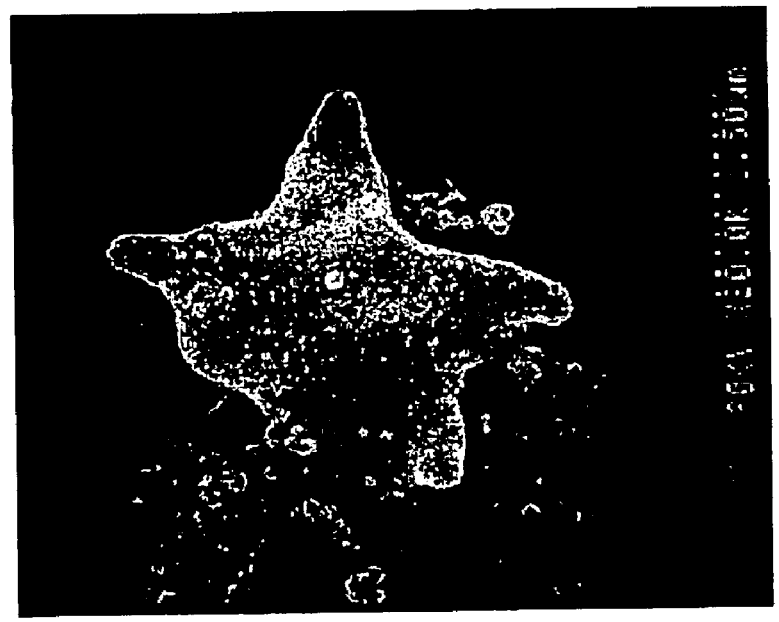

FIGS. 4A–4D depict results of studies of activation of platelets adhered on plates coated with matrix materials as indicated in the different panels A, B, C and D. Panel A: CMC, panel B: CMC-N, panel C: CMC-N/PEO, and panel D: control. Plates (diameter, 18 mm) cast with each matrix were incubated with 2.0 ml of platelet rich plasma having a platelet concentration of 30–35×$10^4/\mu l$ at 37° C. for 20 min. FIGS. 4A–4D depict photomicrographs of platelets which adhered to surfaces comprising CMC (FIG. 4A), CMC-N (FIG. 4B), CMC-N/PEO (FIG. 4C) and control (FIG. 4D). FIG. 4D is a control and shows a platelet having 4 or 5 pseudopods extending from the platelet, indicating that the platelet adhered tightly to the surface. FIG. 4A depicts a platelet adhered to aCMC matrix. As with the control shown in FIG. 4D, this platelet has between 4 and 6 pseudopods. In contrast, the CMC-N adherent platelet (FIG. 4B) has fewer pseudopods (2 or 3), and appear broader. Finally, the platelet adhered to the CMC-N/PEO surface (FIG. 4C) has no pseudopods, indicating that this platelet did not actively adhere to the substrate. Results of these studies are shown in Table 8.

TABLE 8

Adhesion and Activation of Platelets on CMC Derivatized Matrices

| Samples | Platelet adhesion (×10⁶/cm²) | Aggregation |
|---|---|---|
| CMC | 6.3 ± 0.7 | yes |
| CMC-N | 6.9 ± 0.7 | yes |
| CMC-N/PEO | 0.26 ± 0.08 | no |
| Glass | 6.4 ± 1.7 | yes |

Data presented as mean value and standard deviation (n = 5).

We observed no significant differences in platelet adhesion or activation between surfaces of glass and those pre-treated with CMC or CMC-N. However, CMC-N/PEO compositions of this invention showed both substantially decreased platelet adhesion and platelet aggregation compared to CMC, CMC-N and glass alone. Additionally, pseudopod formation by platelets was inhibited by the CMC-N/PEO composites.

Example 16

Thrombin Activity

Thrombin activity was measured in both solution form and after loading to matrices in solid form. To glass tubes containing 1.0 ml fibrinogen (3 mg/ml) in PBS, pH 7.0, we added either 100 μL reconstituted thrombin (40 U) or a piece of thrombin-preloaded matrix. The tubes were incubated at a temperature of 37° C., and the time for a fibrin gel to form was measured according to the methods of Liu (Liu 1999). Reconstituted thrombin solutions were freeze-dried under the same conditions used to prepare thrombin-loaded matrices. The thrombin thus treated was used as a control. Results of these experiments are shown in Table 9.

TABLE 9

Determination of Thrombin Activity in CMC and CMC-N Matrices

| | Clotting time (sec) | |
|---|---|---|
| Samples | Fibrinogen/PBS | Whole blood |
| Thrombin in the form received | 36 ± 2 | 15 ± 6 |
| Thrombin after lyophilization | 50 ± 11 | 23 ± 6 |
| CMC pre-loaded with thrombin | 201 ± 46 | 149 ± 32 |
| CMC-N pre-loaded with thrombin | 153 ± 7* | 113 ± 11 |
| CMC-N/PEO pre-loaded with thrombin | 110 ± 18 | 107 ± 9 |

Data presented as mean value with standard deviation (n = 5); $P < 0.05$;
*$P < 0.1$ in comparing with CMC-N/PEO pre-loaded with thrombin.

Table 9 shows that lyophilization decreased thrombin activity slightly in aqueous solution, as reflected by the increased clotting time compared to unprocessed thrombin. Thrombin activity progressively decreased when it was in a matrix, with the order of decrease: CMC-N>CMC-N/PEO>CMC.

This result indicates that thrombin is more readily adsorbed onto CMC matrices, and is therefore less available in solution to participate in blood clotting reactions. The CMC-N does not have as great a binding to thrombin as CMC does, the CMC-N/PEO matrices bind thrombin to a lesser degree. Therefore, using the compositions of this invention, one can regulate the amount of an active agent (e.g., thrombin or other drug) released into free solution by selecting different compositions of a matrix.

Example 17

Whole Blood Coagulation Time

Hemostatic activity of derivatized CMC matrices were determined by measuring the time required to form a blood clot (thrombus time) in contact with whole, citrated bovine blood. To a borosilicate glass tube containing 100 μL of the matrix, we added 5.0 ml citrate-treated whole blood, which was immediately followed by the addition of 0.5 ml $CaCl_2$ solution (0.25M), and stirred gently, while incubated at a temperature of 37° C. The time required for a clot to form was measured results of these studies are shown in Table 9. As shown by Table 9, the clotting time for each type of matrix was increased, compared to that of either unprocessed (as received from supplier) or after lyophilization. The order of clotting times, in increasing times was: CMC-N>CMC-N/PEO>CMC. Thus, as with the results of thrombin time shown in Table 8, the CMC and derivatized CMC matrices retained thrombin compared to either of the non-matrix bound thrombin preparations.

Example 18

Clotting of a Spurting Bleeding Model

Figure 5:
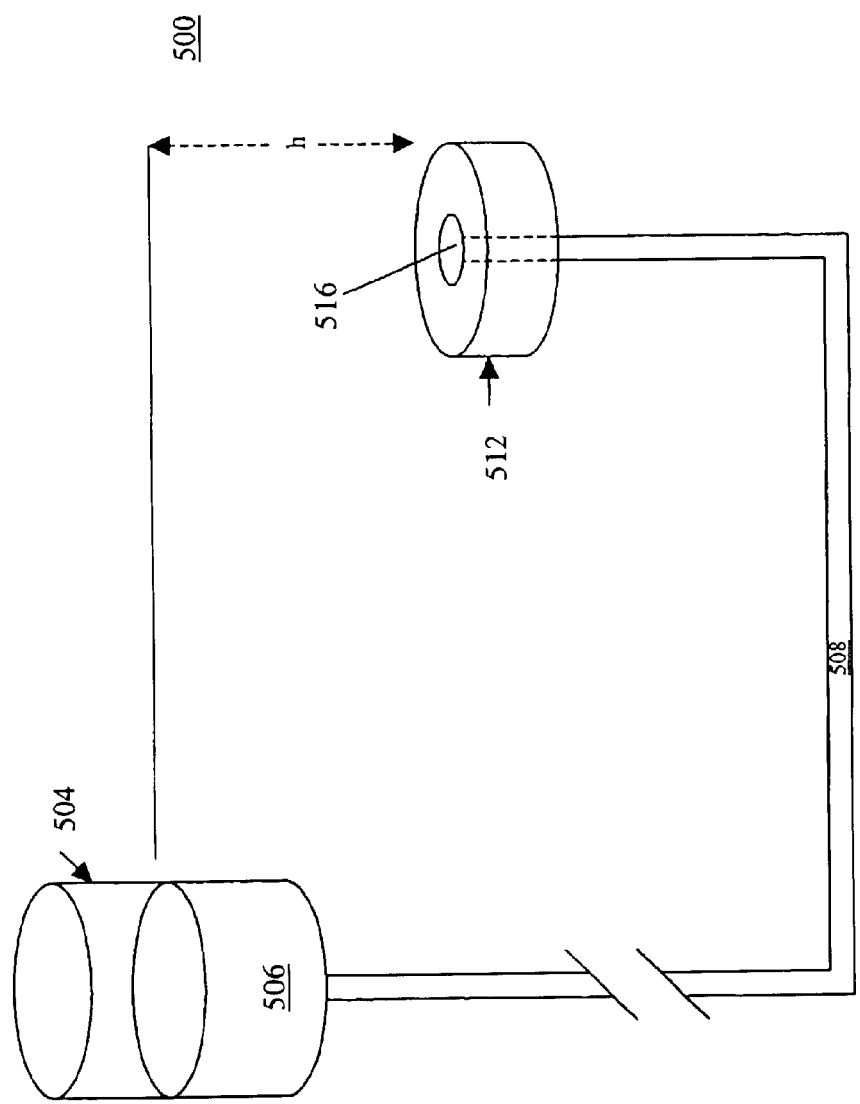
FIG. 5 is a schematic representation of a spurting bleeding model for studying hemostasis. The apparatus consists of a reservoir connected through a tube to a receiver over which porcine skin is stretched.

Matrices were tested in vitro for the potential to stop aggressive bleeding by evaluating the ability to form matrix/fibrin networks and its ability to resist increasing pressure in a spurting bleeding model 500 as shown in FIG. 5. Fibrinogen solution (35 mg/ml, PBS) 506 was pre-incubated at 37±2° C., stored in liquid reservoir 504, which was connected with a PVC tube (i.d. 3.5 mm) 508 through a three-way stopcock (not shown). The other end of the tubing was attached to a circular test panel 512 with a hole (8 mm diameter) 516 in the center. Hairless porcine skin (not shown) was mounted on circular panel and double fastened by cable ties (not shown). Another hole (2 mm diameter; not shown) was created in the skin, positioned 3 mm away from the hole in the test panel. Fibrinogen solution was released to moisten the surface prior to each experiment. Gel sponges of matrices containing either CMC, CMC-N, CMC-N/PEO or control, 100 mg/sponge, were moistened with 200 μl of reconstituted thrombin solution (1000 U/ml) and placed on the top of the hole and the surrounding area. After 2 min, the stopcock was opened and the liquid reservoir was lifted gently. The stopcock was switched back upon leakage of liquid from the hole onto the skin, the height (h) from the exit of test panel to the level of liquid reservoir was recorded and used to calculate the hydrostatic pressure (expressed as mm Hg) applied to the gel covering the hole in the porcine skin. In another experiment, thrombin pre-loaded matrices were tested in the same method as described above.

All experiments for the determination of the haemostatic activity of matrices were carried out three or five times. Data presented as mean value with standard deviation.

Figure 6:
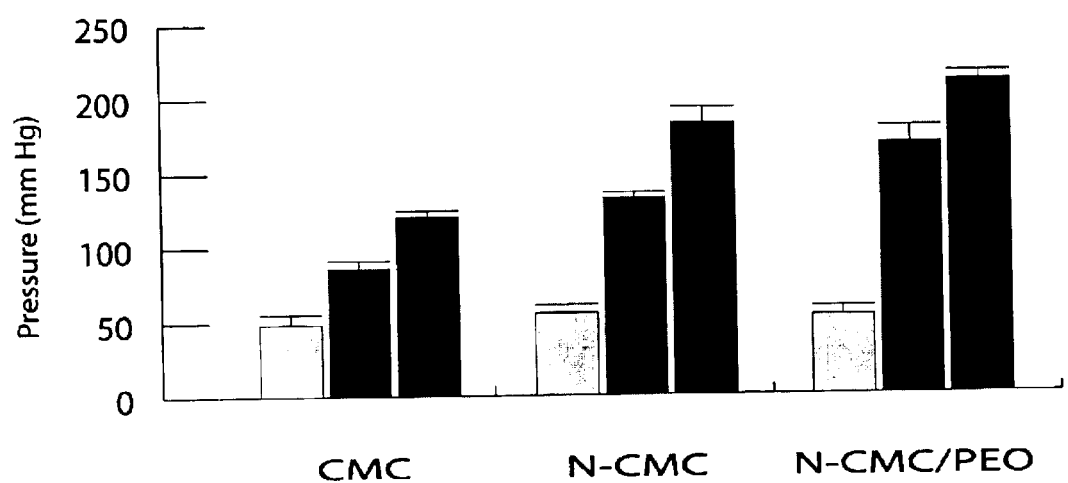
FIG. 6 depicts a graph of results of studies of resistance to spurting bleeding (expressed as mm Hg) of various matrix/thrombin formulations. Data are represented as three groups of three bars each. The left group of three bars represents results obtained using a CMC matrix, the middle group represents results obtained using a CMC-N matrix and the right group represents results obtained using CMC-N/PEO matrices. Within each group, the left bars represent results obtained using matrices alone, the middle bars represent results obtained using matrices with thrombin loaded on site, and the right bars represent results obtained using matrices pre-loaded with thrombin. Specimen of matrix materials used in each test was 100 mg. Thrombin content in each type of matrices was 2 U/mg. Each test was repeated for 5 times, the data expressed as mean±standard deviation. Resistance expressed by using thrombin solution was 15 mm Hg.

FIG. 6 shows the results of these experiments. FIG. 6 is a graph of hydrostatic pressure (in mm Hg) on the vertical axis, as a function of the type of matrix used to cover the pore in the skin. Three sets of three bars each are shown. Each set of bars represents results of studies using matrices containing CMC alone (left group of bars), N-CMC (CMC-N; middle group of bars) and N-CMC/PEO (CMC-N/PEO; right group of bars). Within each group of bars, the left bars (open bars) represent matrix materials alone (e.g., without thrombin). Horizontally hatched bars (middle of each set) represent matrix materials that had been pre-loaded prior to placing the matrix over the skin. Diagonally hatched bars (right of each set) represent matrices onto which thrombin had been placed on site.

In the absence of any matrix material, the thrombin solution alone prevented bleeding to a degree (spurting threshold: about 15 mm Hg). The matrices alone (open bars)

showed somewhat greater ability to prevent spurting, having thresholds of about 45 mm HG (CMC alone), 53 mm Hg (CMC-N alone) and about 52 mm HG (CMC-N/PEO alone).

In contrast, the addition of thrombin to each matrix improved the ability of that matrix to inhibit spurt bleeding. Addition of thrombin pre-loaded into CMC matrices increased spurt threshold to more than a factor of about 2 (e.g., to about 85 mm Hg), and addition of thrombin in situ increased the threshold for spurt bleeding by about 3 fold (to about 120 mm Hg). The results were substantially greater for CMC-N matrices, with the pre-loaded matrix increasing threshold to about 130 mm Hg and the in situ loaded matrix having a threshold of nearly 200 mm Hg. The CMC-N/PEO matrix increased the spurt bleeding threshold even more, with the pre-loaded matrix having a threshold of about 170 mm Hg, and the in situ loaded matrix having a threshold of over 200 mm Hg.

These studies indicated that CMC matrices, whether derivatized or derivatized and conjugated with PEO can increase the hemostatic effects of thrombin substantially. Matrices of this invention can be provided with drugs and can increase the efficacy of hemostatic agents, either when pre-loaded into the matrix, making their manufacture and use easy, or when loaded in situ during surgery. Incorporation of PEO into a CMC matrix can decrease platelet adherence and activation, and can provide a matrix from which pharmacologically active agents may be released and have increased local effects.

IV Drug Delivery Using Derivatized CPS

It can be readily appreciated that any number of drugs, biologicals and other chemical agents can be delivered using the derivatized CPS and PE composites of this invention. Certain agents can be advantageously used for local delivery, providing desired concentration at a desired site, but while decreasing undesirable, systemic effects. Such agents include, but are not limited to therapeutic proteins, such as thrombin to aid in attaining and maintaining hemostasis, growth factors for bone, cartilage, skin and other tissue and cell types. Some of these peptide and protein growth factors include bone morphogenic protein (BMP), epidermal growth factor (EGF), connective tissue growth factor (CTGF), platelet derived growth factor (PDGF), angiotensin and related peptides, and RGD-containing peptides.

Additionally, locally acting drugs include fungicides, histamine, antihistamine, anti-inflammatory drugs (methotrexate), local anesthetics, angiogenesis promoting drugs ( e.g., to treat cardiovascular disease, and anti-angiogenesis factors (e.g., to treat tumors).

DNA-based therapeutics, including antisense DNA, gene therapeutics and RNA-based therapeutics are also suitably delivered using the compositions of this invention. These agents can be used to either inhibit or promote transcription of endogenous genes, or alternatively, can provide exogenous gene products to promote local treatment.

Locally delivered chemotherapeutic agents can also be delivered. These include, by way of example only, antibiotics to treat microbial conditions, antifungal agents, anti-parasitic agents, anti-neoplastic agents including alkylating agents, anti-metabolites and the like.

It can also be appreciated that various hormones and steroids can be delivered, as can other, systemically acting drugs, which can be delivered transmucosally or transdermally. These include IgG, clotting factors and enzymes for treating mucopolysaccharidosis or other conditions.

Cardiovascular drugs include vasodilators such as $\beta$-adrenoreceptor agonists including terbutaline and low-dose epinephrine, $\alpha$-adrenoreceptor antagonists including norepinephrine, high-dose epinephrine and the like, and vasodilators including nitroprusside and nitroglycerin.

Vaccines can be delivered transmucosally or transdermally.

CMC binding therapeutics including proteins and transcription factors), CMC-N binding therapeutics (DNA, cDNA) and other materials capable of being associated with CMC and CMC-N and then released from them. Lipid binding protein, lysosomal encapsulated proteins or drugs can also be advantageously delivered using the derivatized CPS of this invention.

References

Liu L S, Ito Y and Imanishi Y. Synthesis and antithrombogenicity of heparinized polyurethanes with intervening space chains of various kinds. *Biomaterials* 12: 390–396, 1991.

Ito Y, Liu L S, Matsuo R and Imanishi Y. Synthesis and nonthrombogenicity of polymer membrane with surface-grafted polymers carrying thrombin inhibitor. *Journal of Biomedical Materials Research* 26: 1065–1080, 1992.

Liu L S, Thompson A Y, Heidaran Mass., Poser J W and Spiro R C. An osteoconductive collagen/hyaluronate matrix for bone regeneration. *Biomaterials* 20: 1097–1108, 1999.

Rhee W, Rosenblatt J, Castro M, Schroeder J, Rao P R, Harner C H and Berg R A. In vivo stability of poly(ethylene glycol)-collagen composites. In: Harris J M and Zalipsky S, editors. Poly(ethylene glycol) Chemistry and Biological Applications. Washington, D.C.: ACS Press: 1997: pp420–440.

All of the above cited references, and all other references cited herein are fully incorporated by reference in their entirety.

It can be appreciated that the above descriptions and examples are only representative of the scope of this invention. Other embodiments, variations and applications of the derivatized CMCs and matrices can be used without departing from the intent and scope of this invention. Further understanding of the scope of the invention is found in the claims.

INDUSTRIAL APPLICABILITY

The compositions and methods of this invention are useful for controlled drug delivery, hemostatasis and in minimizing surgical adhesions. Derivatizing CMCs with primary amines and/or other types of active moieties can provide improved structural features, including interstitial pores, that can hold biologically active materials and release them under controlled conditions.

We claim:

1. A composition for delivering a drug to a tissue, comprising:
   a derivatized carboxymethylcellulose CMC;
   a polyalkylene oxide (PAO) selected from the group consisting of polyethylene glycol (PEG) and polyethylene oxide (PEO); and
   a drug.

2. The composition of claim 1, further comprising underivatized CMC.

3. The composition of claim 2, wherein said derivatized CMC is carboxymethyl cellulose having a primary amine (CMC-N).

4. The composition of claim 1, wherein said drug is thrombin.

5. The composition of claim 1, wherein said derivatized CMC is CMC-N.

6. A hemostatic composition, comprising:
CMC-N;
PEO; and
thrombin.

7. The composition of claim 6, further comprising a vasoconstrictor.

8. A composition comprising:
a positively charged derivatized CPS;
a negatively charged derivatized CPS;
a neutral CPS; and
a PAO.

9. A method of manufacturing a composition, comprising the steps of:
(a) providing a solution comprising a CMC;
(b) providing a derivatizing agent;
(c) reacting said CMC and said derivatizing agent to produce a solution containing a derivatized CPS; and
(d) adding a PAO to said solution containing said derivatized CMC.

10. The method of claim 9, further comprising the step of adding a drug to said solution obtained in step (d).

11. The method of claim 10, wherein said drug is a hemostatic drug.

12. The method of claim 9, wherein said derivatizing agent is selected from the group consisting of diamines, sulfonyl chlorides, vinyl sulfones and periodates.

13. The method of claim 9, wherein said derivatized CMC has a molar ratio of carboxylic acid residues available for derivatization to the number of derivatizing molecules is in the range of about 1 to about 50.

14. The method of claim 13, wherein the molar ratio of carboxylic acid residues available for derivatization on said CMC to the number of derivatizing molecules is in the range of about 20 to about 50.

15. The method of claim 13, wherein the molar ratio of carboxylic acid residues available for derivatization on said CMC to the number of derivatizing molecules is in the range of about 1 to about 20.

16. The method of claim 12, wherein said derivatizing agent is trifluoroethanesulfonyl chloride.

17. The method of claim 12, wherein said derivatizing agent is selected from the group consisting of vinyl chloride and divinyl chloride.

18. The method of claim 17, wherein a ratio of available hydroxyl residues on said CMC to said derivatizing agent is in the range of about 30:1.

19. The method of claim 9, wherein said derivatizing agent comprises a linker having a reactive moiety at each end of said linker.

20. The method of claim 19, wherein said linker has a length of about 2 to about 10 atoms.

21. The method of claim 19, wherein said linker has a length of about 3 to about 8 atoms.

22. The method of claim 19, wherein said linker has a length of about 5 to about 7 atoms.

23. The method of claim 19, wherein said linker has a length of about 6 atoms.

24. The method of claim 9, further comprising the step of drying said composition to form a dried membrane.

25. The method of claim 10, further comprising the step of drying said composition to form a dried membrane.

26. The method of claim 9, wherein said derivatized CMC is CMC-N.

27. The method of claim 10, wherein said derivatized CMC is CMC-N.

28. The method of claim 9, where in said PAO is PEO.

29. The method of claim 10, wherein said PAO is PEO.

30. A method of manufacturing a hemostatic composition, comprising the steps of:
(a) providing a solution comprising CMC-N;
(b) providing a solution comprising PEO;
(c) mixing said solution of CMC-N and said solution of PEO together to form a CMC-N/PEO solution; and
(d) adding a hemostatic drug to said CMC-N/PEO solution.

31. The method of claim 30, further comprising drying said CMC-N/PEO solution to form a dried membrane.

32. A method for decreasing post-surgical adhesions, comprising the steps of:
(a) providing a composition of:
a derivatized CMC; and
a PAO; and
(b) applying said composition to a surgical site.

33. A method for promoting hemostasis, comprising the steps of:
(a) providing a composition of:
a derivatized CMC;
a PAO; and
a hemostatic drug; and
(b) applying said composition to a site of bleeding.

34. The method of claim 30, wherein said hemostatic drug is selected from the group consisting of clotting agents and vasoconstrictors.

35. The method of claim 30, wherein said drug is thrombin.

36. The method of claim 30, further comprising the step of applying pressure to said site of bleeding.

37. A composition comprising:
a positively charged derivatized CPS;
a negatively charged CPS; and
a PAO.

38. A method for promoting hemostasis, comprising the steps of:
(a) providing a composition of:
CMC-N;
PEO; and
thrombin; and
(b) applying said composition to a site of bleeding.

39. The method of claim 38, wherein said site of bleeding is associated with trauma, surgery, arthroscopy of laparoscopy.

40. The method of claim 39, wherein said site of bleeding is associated with surgery to inhibit formation of adhesions.

41. The method of claim 39, wherein said site of bleeding is associated with surgery to inhibit adhesion reformation.

42. The composition of claim 6, wherein said thrombin is recombinant human thrombin.

43. The composition of claim 1, wherein said derivatized CMC comprises a CMC and one or more members of the group consisting of primary amines, sulfonyl chlorides, tresyl chlorides, aldehydes and vinyl sulfones.

44. The composition of claim 1, wherein said derivatized CMC comprises a CMC and a moiety comprising a linker and an active moiety at each end of said linker.

45. The composition of claim 1, wherein said derivatized CMC comprises a CMC and a primary amine.

46. The composition of claim 44, wherein said linker has a length of about 2 to about 10 atoms.

47. The composition of claim 44, wherein said linker has a length of about 3 to about 8 atoms.

48. The composition of claim 44, wherein said linker has a length of about 5 to about 7 atoms.

49. The composition of claim 44, wherein said linker has a length of about 6 atoms.

50. The composition of claim 1, wherein said derivatized CMC has a molar ratio of carboxlic acid residues to the number of derivatizing molecules is in the range of about 1 to about 50.

51. The composition of claim 1, wherein said derivatized CMC has a number of derivatized moieties in the range of about 1 to about the maximum number of carboxylic acid residues on said CMC available for derivatization.

52. The composition of claim 1, wherein said derivatized CMC has reactive moieties formed by way of one or more chemicals selected from the group consisting of carbodiimides, active esters, active aldehydes and carbonylating agents.

53. The composition of claim 52, wherein said carbodiimide is 1-Ethyl-3-(3-dimethylaminopropyl)carbodiimide hydrochloride (EDC).

54. The composition of claim 1, wherein said derivatized CMC comprises aldehydes.

55. The composition of claim 1, wherein said derivatized CMC has hydroxyl groups derivatized sulfonyl groups attached thereto.

56. The composition of claim 54, wherein said sulfonyl group comprises a moiety selected from the group consisting of vinyl sulfones and triflurorethanesulfonyl chlorides.

57. The composition of claim 1, wherein said composition is dried to form a membrane.

* * * * *